United States Patent [19]

Springer et al.

[11] 4,223,293

[45] Sep. 16, 1980

[54] TERMINAL PIN ARRANGEMENT FOR AN EXHAUST GAS SENSOR

[75] Inventors: Jerry L. Springer; Charles M. Wells, both of Livonia; William F. Horn, Plymouth, all of Mich.

[73] Assignee: Ford Motor Company, Dearborn, Mich.

[21] Appl. No.: 5,420

[22] Filed: Jan. 22, 1979

[51] Int. Cl.$^3$ .............................................. H01L 7/00
[52] U.S. Cl. .................................. 338/34; 73/27 R; 324/65 P; 338/229
[58] Field of Search .......................... 338/34, 28, 229; 73/27 R; 324/65 P; 422/98; 23/232 E; 29/610, 612, 613, 619

[56] References Cited

U.S. PATENT DOCUMENTS

| | | | |
|---|---|---|---|
| 3,886,785 | 6/1975 | Stadler et al. | 73/23 |
| 3,932,246 | 1/1976 | Stadler et al. | 338/34 X |
| 4,001,758 | 1/1977 | Esper et al. | 338/34 |
| 4,012,709 | 3/1977 | Logothetis et al. | 338/34 |
| 4,130,797 | 12/1978 | Hattori et al. | 338/34 X |

*Primary Examiner*—C. L. Albritton
*Attorney, Agent, or Firm*—Robert W. Brown; Clifford L. Sadler

[57] ABSTRACT

An improved exhaust gas oxygen sensor of the type adapted for installation in the exhaust conduit of an internal combustion engine. The improved sensor preferably uses a titania metal oxide ceramic element to sense the partial pressure of oxygen in the exhaust gases to which the sensor is exposed. The sensor has a steel body, a ceramic insulator which is used to support the titania sensing element and its wires which pass through the insulator bodies and as terminal pins inserted into enlarged passages in the insulator for connection to the titania sensing element wires. The terminal pins are of an improved design wherein a cement material in the enlarged passage of the insulator is made to flow into a groove in each of the terminal pins and into another space between the exterior of the terminal pin and the interior of the insulator passage. The cement material causes the bond to form between the terminal pin and the insulator and prevent leakage of exhaust gases from the exhaust conduit to flow through the sensor to the ceramic environment. Seepage of the cement material in a location to the terminal pin and its exterior contact point with the insulator also is prevented.

6 Claims, 4 Drawing Figures

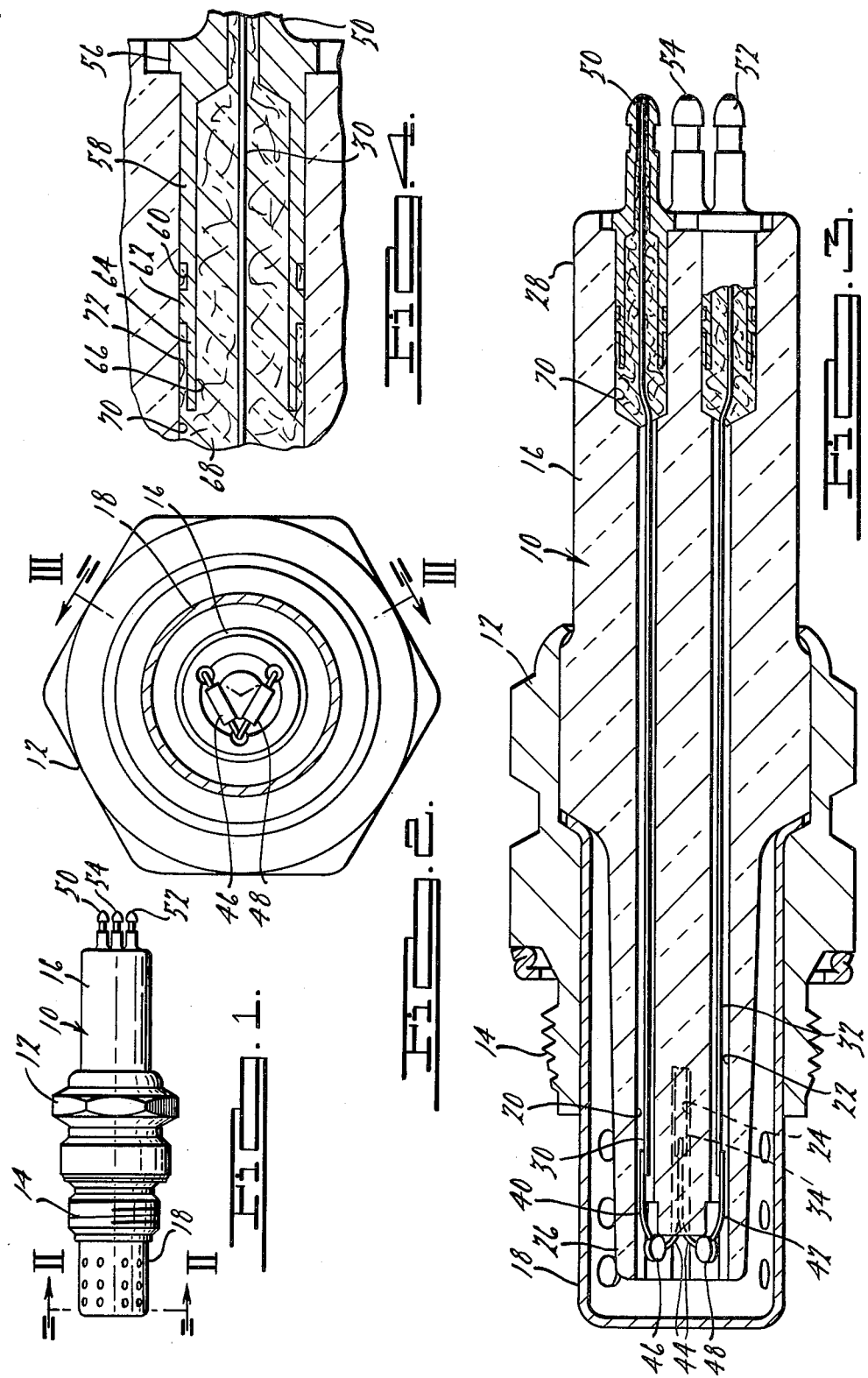

TERMINAL PIN ARRANGEMENT FOR AN EXHAUST GAS SENSOR

CROSS REFERENCE TO RELATED APPLICATIONS

This invention is related to commonly-assigned U.S. Pat. No. 4,001,758 issued Jan. 4, 1977 to M. J. Esper, W. L. Greene, S. R. Merchant, and Charles M. Wells, the latter being one of the present inventors. The invention also is related to commonly-assigned U.S. Patent Application Ser. No. 839,704 filed Oct. 5, 1977 on the names of M. J. Cermak and S. R. Merchant and entitled "Temperature Compensative Resistive Exhaust Gas Sensor Construction".

BACKGROUND

This invention relates to an improved exhaust gas oxygen sensor of the type adapted for installation in a conduit for conveying exhaust gases from an internal combustion engine. The improved sensor is responsive to the partial pressure of oxygen in the exhaust gases to which the sensor is exposed and has an electrical characteristic which varies, when the sensor is at operating temperatures in the range from about 350° C. to about 850° C., with the partial pressure of oxygen in the exhaust gases.

Exhaust gas sensors of the type to which the improvement of the present invention is directed have been fabricated using a titania oxygen sensing element of discshape. The titania element has electrode wires embedded in it for conveying to an electronic control system an electrical signal resulting from variation in the electrical resistance of the titania disc. This variation occurs as the composition of the exhaust gases from an internal combustion engine is varied. The sensor electrical lead wires and the sensor itself are supported by a ceramic insulator mounted within a steel body that is attached to the exhaust conduit from the engine. As the sensor is subjected to exhaust gases of varying compositions, the varying electrical signal generated by the sensor passes through the lead wires in the ceramic insulator to terminal pins at one end of the insulator.

In the prior art exhaust gas oxygen sensor designs, such as those illustrated in the commonly assigned patent and patent application referenced above, the terminal pins have been held in place with a cement material which would seep out of a space between the terminal pins and the ceramic insulator. Also, the terminal pins would become loose after being subjected repeatedly to the temperature variations and conditions that occur in the use of an exhaust gas sensor in a motor vehicle. In this regard, it may be appreciated that an exhaust gas sensor, including its ceramic insulator and terminal pins, is repeatedly heated to high temperatures and then cooled to atmospheric conditions during ordinary use of a motor vehicle in which the sensor may be installed. The exhaust system of an internal combustion engine itself is a severe environment and that, coupled with the temperature cycling just mentioned, has tended to result in weakening and failure of the bond formed between the terminal pins and the ceramic insulators.

SUMMARY OF THE INVENTION

According to the invention, an improved exhaust gas oxygen sensor is provided with terminal pins of improved design which prevent the seepage of cement material from a location between the terminal pin shoulder and the point at which it contacts the ceramic insulator receiving the terminal pin. Also, a better seal between the terminal pins and the enlarged passages in the insulator is provided to prevent leakage of exhaust gases through this area of the exhaust gas sensors. A better bond also is formed between the terminal pins and the insulator.

An improved exhaust gas oxygen sensor according to the invention includes a body adapted for connection to the exhaust conduit of the internal combustion engine. An oxygen sensing element having a plurality of lead wires is provided as is a ceramic insulator having a projecting portion for supporting the oxygen sensing element and having a portion for receiving terminal pins. The projecting portion of the ceramic insulator is adapted to project into the exhaust conduit of an engine when the exhaust gas sensor body is connected thereto as adapted for this purpose. The projecting portion of the insulator also has a plurality of passages therein which extend from the projecting portion to the terminal-pin portion of the insulator. The terminal-pin portion of the passages is enlarged to receive terminal pins of cross-section corresponding to that of the enlarged passages. The oxygen sensing element is supported by the projecting portion of the insulator and has a plurality of its lead wires extending through the passages in the insulator to the terminal pins.

The terminal pins, equal in number to the passages in the insulator and adapted to be received therein, are provided. Each of the terminal pins has a shoulder portion that is located on the exterior of the insulator when the terminal pin is received within the enlarged portion of one of the passages therein. A second portion of each terminal pin is also located within the enlarged portion of the passage and is in contact with its interior surface. The terminal pin also has a third portion located in the enlarged portion of the insulator passage but not in contact therewith.

A cememt material is provided in each of the enlarged portions of the passages in the insulator. The cememt material bonds the terminal pin to the insulator and also forms a seal preventing leakage of exhaust gases as is described above. The cememt material is located between the third portion of the terminal pin and the interior surface of the enlarged passage of the insulator in which the terminal pin is located.

The third portion of each of the terminal pins may be a surface of reduced diameter, as compared to a corresponding diameter of the enlarged portion of the insulator passage. Furthermore, the third portion of the terminal pin may take the form of a groove in the terminal pin which is followed by a fourth portion of the terminal pin that is in contact with the inside surface of the insulator passage and that is followed, in a location more remote from the shoulder portion of the terminal pin than is the fourth portion, by a fifth portion which is not in contact with the inside surface of the insulator passage.

These and other features of the invention may be better understood by reference of the detailed description which follows and to the drawings.

BRIEF DESCRIPTION OF THE DRAWINGS

FIG. 1 is an elevational view of a titania exhaust gas oxygen sensor suitable for installation in the intake manifold of an internal combustion engine;

FIG. 2 is a sectional end view, taken along the line II—II in FIG. 1, and is shown in enlarged scale;

FIG. 3 is a sectional view, taken along the line III—III of FIG. 2, showing the internal structure of the sensor of FIGS. 1 and 2 and also in an enlarged scale; and FIG. 4 is a further enlarged sectional view of a portion of one of the terminal pins in the exhaust gas sensor of FIG. 3.

DETAILED DESCRIPTION

With particular reference now to the drawings, wherein like numerals refer to like parts in the several views, there is shown a complete titania exhaust gas sensor assembly generally designated by the numeral 10. The sensor 10 includes a steel body 12, which may be substantially identical to a spark plug body, having a threaded portion 14 for engagement with a suitable threaded aperture provided within the exhaust system or exhaust conduit of an internal combustion engine (not shown). In most cases, the sensor 10 would be installed in an aperture in a location in the exhaust manifold or conduit near the flange that would connect to an exhaust pipe. A ceramic insulator 16 of circular cross-section extends through the body 12 and has a tapered portion 26 projecting outwardly from the body 12 into the volume defined by the boundaries of a perforated protection tube 18. The projecting portion 26 of the insulator, among other things, acts as a support structure for an oxygen sensing element 46 and a thermistor 48. There are three longitudinal passages 20, 22 and 24 extending from the projecting end or portion 26 of the ceramic insulator to its opposite terminal-pin portion of end 28. Wires 30, 32 and 34 are located in the respectively corresponding passages 20, 22 and 24 and are of a heat resistant character, preferably being made from an alloy as as 80% nickel-20% chromium wire. These electrically conductive wires are welded to precious-metal wire leads 40, 42 and 44, which are embedded in the disc-shaped ceramic, metal oxide, oxygen sensing and thermistor elements 46 and 48.

Element 46 is a ceramic titania $O_2$ sensor responsive to the partial pressure of oxygen in the gaseous medium to which this element is exposed. Sensor element 46 may be fabricated in accordance with the teachings of commonly-assigned U.S. Pat. No. 3,886,785 issued June 3, 1975 and U.S. Pat. No. 3,932,246 issued Jan. 13, 1976, both in the names of Stadler et al. With regard to the fabrication of the oxygen sensing element 46, it is suggested that consideration be given to the teachings of commonly-assigned and previously or concurrently-filed patents, relating to exhaust gas sensors or thermistors, expected to issue subsequent to the filing date of this patent application.

The element 48 is a thermistor. The thermistor may be made from titania ceramic material of greater density, near its theoretical density, than the density of the porous titania oxygen sensor 46. Alternatively, the thermistor 48 may be constructed in accordance with the teachings of copending and commonly-assigned U.S. patent application Ser. No. 857,498 filed Dec. 5, 1977 in the names of Logothetis, Laud and Park and entitled "Rare Earth-Yttrium, Transition Metal Oxide Thermistors". The thermistor 48 is intended to provide temperature compensation in accordance with the circuitry best described in commonly-assigned, concurrently-filed U.S. patent application Ser. No. 5,422 entitled "Exhaust Gas Sensor Electrical Circuit Improvement".

The sensor of FIGS. 1 through 4 is intended to be used in conjunction with electronic circuitry for closed-loop feedback control of the amount of fuel supplied to an internal combustion engine. The sensor indicates whether the exhaust gases contain a substantial amount of HC and CO or whether instead there is a substantial amount of $CO_2$, $H_2O$ and $O_2$, thereby indicating whether or not the air/fuel ratio of the mixture supplied to the engine was rich or lean with respect to the stoichiometric value of about 14.7 parts of air to each part of fuel by weight. This air/fuel ratio typically is expressed as a normalized air/fuel ratio lambda, wherein the actual ratio is divided by the stoichiometric value and the stoichiometric ratio therefore is represented as 1.0 in accordance with well-known practice.

The exhaust gas sensor 10 has terminal pins 50, 52 and 54 designed for connection to external circuitry as specified above to enable it to be used in a feedback fuel control system.

The ceramic metal oxide elements 46 and 48 and the remainder of the exhaust gas oxygen sensor 10, including its terminal pins 50, 52 and 54 in the ceramic insulator 16, are intended to operate over a temperature range extending from about 350° C. to 850° C. These elevated temperatures are produced primarily as a result of the location of the exhaust gas oxygen sensor 10 in the exhaust stream of an internal combustion engine. The sensor, therefore, is subjected repeatedly to wide variations in temperature. When installed in a motor vehicle the sensor 10 may be subjected to environmental temperatures as low as −40° C. When the vehicle is placed in operation, this temperature may rise to 500° or 600° C. in a very short time. Cyclical heating and cooling of the sensor 10 may occur several times each day in typical motor vehicle usage. This environment is very hostile with respect to the bond formed between the terminal pins 50, 52 and 54 and the ceramic insulator 16 in which they are received.

The improved terminal-pin arrangement of the invention is best seen in FIG. 3 and in the further enlarged sectional view of FIG. 4, which illustrates in greater detail the terminal pin 50. As was described in the aforementioned U.S. Patent Application Ser. No. 839,704, a Sauereisen number 31 acid-proof cement, a hardenable ceramic cement and sealant material that is commercially available, is used in the enlarged terminal-pin portion 68 of the ceramic insulator 16. The Sauereisen cement partially fills the enlarged terminal-pin portion of each of the passages 20, 22 and 24. For convenience herein, the interior walls or surfaces of the enlarged portion of the passages are designated by the numeral 70.

The pin 50, as does each of the pins 52 and 54, has a shoulder 56 that is in contact with the insulator 16 in the location next to the lip of the enlarged portion 68 of the passage 20 in which the terminal pin 50 is received. The terminal pin 50 has a series of four interconnected portions 58, 60, 62 and 64 each of which is more remotely removed from the shoulder 56 than is the preceding portion.

The shoulder portion 56 of the terminal pin 50 may seem to be of larger diameter than is the diameter of the enlarged portion 68 of the passage 20. On the other hand, the second portion 58 of the terminal pin 50 is sized to fit within the contact the inside surface 70 of the enlarged portion 68. Portion 60 of the terminal pin also is received within the enlarged portion of the passage, but is of smaller diameter. This third portion 60 of the terminal pin may be followed by portions 62 and 64. Terminal pin portion 62 is of a diameter substantially equal to the diameter of the inside surface 70 of the passage and, therefore, the third portion 60 of the terminal pin is a groove. Portion 64 is of reduced diameter as compared to portion 62.

In the prior design of the titania exhaust gas sensor depicted in the aforementioned patent application Ser. No. 839,704, the terminal pins are of straight-sided configuration. The improved terminal pin 50 is hollow throughout its length, as was the prior pin design, but has the reduced cross-section surfaces 60 and 64 as shown particularly in FIG. 4. With the prior design, the cement located within the enlarged portion 68 of the passage had a tendency to seep out of the insulator in the region between the outer diameter of the straight-sided terminal pin and the shoulder portion thereof. With the improved exhaust gas sensor design of the invention, the terminal pin 50, when inserted into the insulator 16, permits the cement material in the enlarged portion 68 of the insulator to enter the center hollow portion of the terminal pin where it surrounds the sensor element lead wire 30 that passes through the terminal pin.

Upon insertion of the terminal pin 50 into the enlarged passage, a portion of the cement material passes into the region 72 between the exterior of the fifth portion 64 of the terminal pin and the inside surface 70 of the passage. The cement material may then flow past the portion 62 of the terminal pin so that a slight amount thereof can enter the groove formed at portion 60 of the terminal pin. This groove acts as a well that prevents the cement material from passing the lip 62 of the terminal pin and thereby prevents seepage from the space between the shoulder 56 and the insulator 16. Also, the cement material forms a seal that prevents exhaust gases within the passage 20 from being transferred via the terminal pin, to the environment exterior of the exhaust gas sensor.

When the cement material hardens, it has been found that a better bond is achieved with the terminal pin design 50 than has been the case with prior terminal designs. In contrast to the prior design, this terminal pin design and its attachment to the ceramic insulator 16 has been found to surpass the applicable specifications pertaining to exhaust gas leakage both before and after 50,000 miles of durability testing.

After the terminal pins are inserted in and bonded to the ceramic insulator, the lead wires are welded or otherwise electrically connected to the associated terminal pins at their respective tips.

Based upon the foregoing description of the invention, what is claimed is:

1. An improved exhaust gas oxygen sensor of the type adapted for installation in a conduit for conveying exhaust gases from an internal combustion engine, the improved sensor being responsive to the partial pressure of oxygen in the exhaust gases to which the sensor is exposed and having an electrical characteristic which varies, when the sensor is at operating temperatures in the range from about 250° C. to about 850° C., with the partial pressure of oxygen in the exhaust gases, the improved sensor comprising:

a body adapted for connection to the exhaust conduit of an internal combustion engine;

an oxygen sensing element having a plurality of lead wires;

a ceramic insulator having a projecting portion for supporting the oxygen sensing element and having a terminal-pin portion for receiving terminal pins, the projecting portion being adapted to project into the exhaust conduit when the body is connected thereto as adapted therefor, the projecting portion of the insulator having a plurality of passages therein extending from the projecting portion to the terminal-pin portion of the insulator, the terminal-pin portion of such passages being enlarged to receive terminal pins, the oxygen sensing element being supported by the projecting portion of the insulator and having a plurality of its lead wires extending through the passages in the insulator;

a plurality of terminal pins received in the insulator, each of the terminal pins having a shoulder portion located exterior of the enlarged portion of one of the passges therein, a second portion received within the enlarged portion of the passage and in contact therewith, and a third portion also received in the enlarged portion of the passage but not in contact therewith, the terminal pins being electrically connected to the wires in the passages; and a cement material in the enlarged portions of each of the passages in the insulator, the cement material bonding the terminal pins to the insulator, the cement material being located within the space formed between the third portion of the terminal pin received in the enlarged portion of the passage but not in contact therewith, the cememt in such location providing a seal, whereby, leakage of exhaust gases, from the exhaust conduit to its surrounding environment via the terminal pins, is prevented.

2. An improved exhaust gas oxygen sensor according to claim 1, wherein each of the terminal pins is hollow and has one of the lead wires from the oxygen sensing element passing through its hollow portion, the cement material in each of the enlarged portions of the insulator passages being received within the hollow portion of the terminal pin and surrounding the lead wire therein.

3. An improved exhaust gas oxygen sensor according to claim 2, wherein the electrical lead wires in the terminal pins are welded thereto to form electrical contact therewith.

4. An improved exhaust gas oxygen sensor according to claim 2, wherein each of the terminal pins includes a fourth portion received within the enlarged portion of the insulator passage, the third portion of the terminal pin being a groove located between the second and fourth portions thereof and the cement material within the enlarged portion of the insulator passages being located in the groove of the terminal pins.

5. An improved exhaust gas oxygen sensor according to claim 4, wherein each of the terminal pins in the enlarged portions of the passages in the insulator has a fifth portion located more remote from the shoulder portion of the terminal pin that is the fourth portion and of a smaller cross-section than the passage in which it is located, whereby, the cement material in the passage is located between the fifth portion of the terminal pin and the interior of the passage.

6. An improved exhaust gas oxygen sensor according to claims 4 or 5 wherein the groove in the terminal pin acts as a well for receipt of the cement material, whereby, when pressure is applied to the terminal pin during its insertion within the enlarged portion of the passage in the insulator, the cement material rises up the interior of the terminal pin and also on the exterior of the terminal pin in the region between the exterior of the terminal pin and the interior surface of the insulator passage, the cement material reaching the groove of the terminal pin and not rising substantially beyond this location, thereby, to prevent seepage of the cement material at the shoulder of the terminal pin where it contacts the insulator.

* * * * *